United States Patent
Giuliani

(10) Patent No.: US 9,622,904 B2
(45) Date of Patent: Apr. 18, 2017

(54) THERAPEUTIC COLLAR

(71) Applicant: Neuron Guard S.r.l., Modena (IT)

(72) Inventor: Enrico Giuliani, Modena (IT)

(73) Assignee: Neuron Guard S.r.l., Modena (IT)

( * ) Notice: Subject to any disclaimer, the term of this patent is extended or adjusted under 35 U.S.C. 154(b) by 0 days.

(21) Appl. No.: 14/633,824

(22) Filed: Feb. 27, 2015

(65) Prior Publication Data

US 2015/0238349 A1    Aug. 27, 2015

Related U.S. Application Data

(63) Continuation-in-part of application No. PCT/IB2013/059262, filed on Oct. 10, 2013.

(30) Foreign Application Priority Data

Oct. 10, 2012   (IT) ............................. MO2012A0246

(51) Int. Cl.
     *A61F 7/00*      (2006.01)

(52) U.S. Cl.
     CPC ........ *A61F 7/00* (2013.01); *A61F 2007/0009* (2013.01); *A61F 2007/0012* (2013.01); *A61F 2007/0056* (2013.01); *A61F 2007/0075* (2013.01); *A61F 2007/0095* (2013.01)

(58) Field of Classification Search
     CPC ...... A61F 2007/0011; A61F 2007/0012; A61F 2007/001; A61F 2007/0009; A61F 5/055; A61F 2007/0075; A61F 2007/0095; A61F 2007/0056; A61F 5/05883
     USPC .......................................................... 602/18
     See application file for complete search history.

(56) References Cited

U.S. PATENT DOCUMENTS

| 5,086,629 | A | | 2/1992 | Dibrell |
| 5,603,728 | A | * | 2/1997 | Pachys ................ A61F 7/02 607/104 |
| 5,823,984 | A | | 10/1998 | Silverberg |

(Continued)

FOREIGN PATENT DOCUMENTS

| CZ | 20100645 A3 | 3/2012 |
| DE | 102005044402 A1 | 3/2007 |

(Continued)

OTHER PUBLICATIONS

International Search Report for Application No. PCT/IB2013/059262, mailed on Mar. 11, 2014, pp. 1-4.

(Continued)

*Primary Examiner* — Kari Rodriquez
(74) *Attorney, Agent, or Firm* — Intellectual Innovations Legal Advisors

(57) ABSTRACT

A therapeutic collar comprising an elongate body made from a flexible material for extending around at least a portion of the neck of a patient. The body has a length approximating the circumference of the neck, two thermoelectric devices for overlying two carotid arteries in the neck and two thermoelectric devices for overlying of two vertebral arteries in the neck when the elongate body is secured around the neck of the patient. At least one cooling tube is carried by the elongate body and extends in the vicinity of each of the thermoelectric devices for removing heat from the thermoelectric devices.

20 Claims, 4 Drawing Sheets

(56) References Cited

U.S. PATENT DOCUMENTS

| | | | |
|---|---|---|---|
| 2005/0149153 A1* | 7/2005 | Nakase | A61F 7/02 607/108 |
| 2008/0269852 A1* | 10/2008 | Lennox | A61F 7/02 607/104 |
| 2010/0152821 A1* | 6/2010 | Rein | A61F 7/007 607/96 |
| 2010/0198322 A1 | 8/2010 | Joseph et al. | |
| 2012/0143110 A1* | 6/2012 | Maher | A61F 5/055 602/14 |
| 2013/0072776 A1 | 3/2013 | Fujii et al. | |
| 2014/0039365 A1* | 2/2014 | Maher | A61F 7/0085 602/2 |

FOREIGN PATENT DOCUMENTS

| | | |
|---|---|---|
| DE | 202011101309 U1 | 11/2011 |
| WO | WO-2006110405 A2 | 10/2006 |
| WO | WO-2006126059 A1 | 11/2006 |

OTHER PUBLICATIONS

Written Opinion for Application No. PCT/IB2013/059262, mailed on Mar. 11, 2014, pp. 1-8.

* cited by examiner

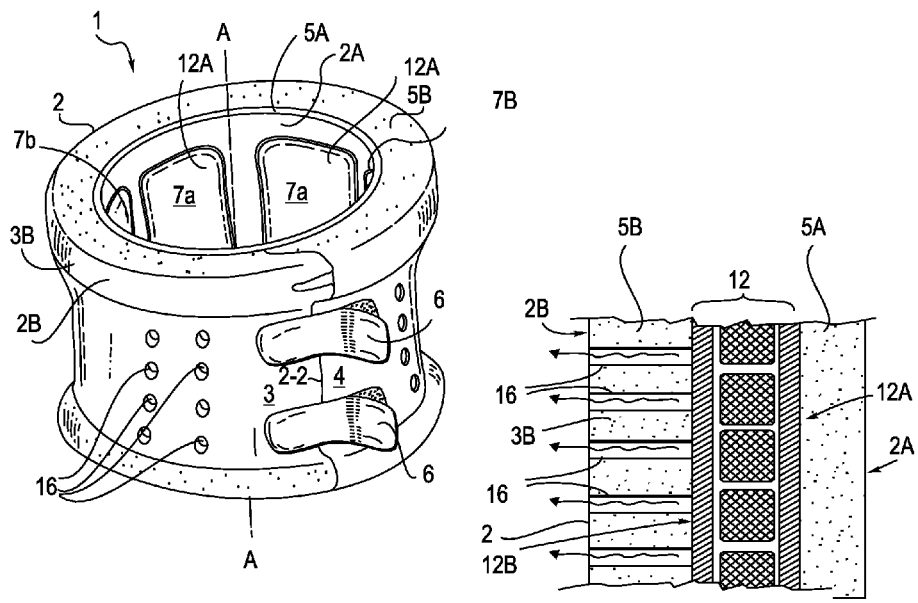
FIG. 1
FIG. 3
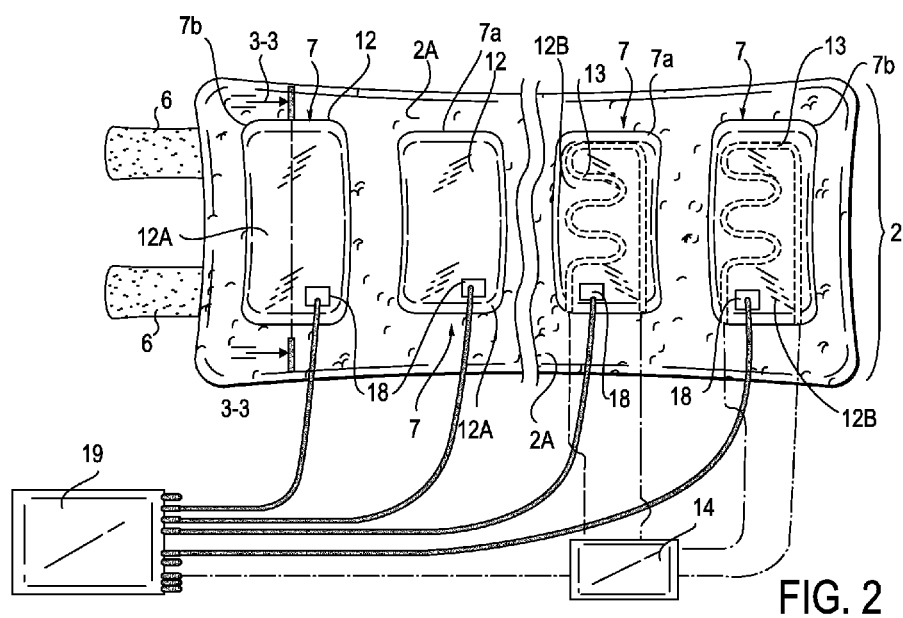
FIG. 2

THERAPEUTIC COLLAR

CROSS REFERENCE TO RELATED APPLICATION

This application is a continuation in part of International Application Number PCT/IB2013/059262 filed Oct. 10, 2013, which claims priority to Italian Patent Application No. MO2012A000246 filed Oct. 10, 2012, the entire content of each of which is incorporated herein by this reference.

FIELD OF THE INVENTION

The invention relates to a therapeutic collar, more particularly to a therapeutic collar for cooling a patient's neck.

BACKGROUND OF THE INVENTION

Collars have been provided for use with severe trauma patients. Some of these collars have a structure that immobilizes or restricts the movements of the head relative to the spine, such that no externally-induced or patient-induced hazardous movements might endanger the overall patient's safety. In practice, such collars can inhibit or limit head movements, for example prevent reclination or upward rotation of the head beyond a given angle relative to the spine, and limit crush or sprain injuries to vertebrae and cervical nerves due to external impact trauma or a cervical disease. Typically, these collars are used on patients involved in road accidents to prevent movements during transportation to hospital or during later convalescence from further worsening any injury suffered due to the accident. Some of such collars are formed from two semi-annular portions which are mutually articulated to open apart for application to the neck, and to close for maintaining the correct position of the neck and head relative to the spine.

Collars are also known that have a semi-rigid structure, typically made of synthetic foam material, to act as transition supports from rigid-collar therapy to the end of the therapy. With time, these collars have been also used in other forms of therapy, such as those for thermal treatment of the circulatory system of the neck that supplies blood to the brain. In practice, apertures can be formed in such collars, namely in the throat section thereof, for introduction and stable but removable positioning of corresponding cooling elements, which have been previously placed and maintained in a refrigerating unit. Such cooling elements can release cold during use, and can be positioned at the carotid artery, the artery that supplies blood to the brain and extends through the front area of the neck, when such collars are closed around the neck.

A cooling collar of the foregoing type is disclosed in International Publication Number WO2012/058427, which teaches an "Immobilization collar with cooling elements and method of using the same". The collar is actually a cervical immobilizer that has an annular support structure having an axial length and at least two support structures. The collar has a front opening that may be closed by a door having a pressure member on the inner neck-facing surface. This pressure member can press a cooling element against the front portion of the patient's neck, which cooling element is inserted between the collar and the neck through the front opening.

The foregoing collars suffer from a number of drawbacks. A first drawback is that such collars that are used for first rescue of patients have a rigid structure, which is specially designed to inhibit any movement of the neck and spine in the proximity of the cervical vertebrae when this part of the body suffers from a traumatic injury or a bone disease. A second drawback is that the cooling elements that are used therein have a temporary effect that progressively decreases with time, especially because they are taken out of the refrigerator and placed in contact with the warm epidermis of the neck. Therefore, the cooling elements must be replaced after a certain time interval to maintain a desired low temperature value required by the therapeutic needs of patients. The replacement of these cooling elements is considerably uncomfortable for patients that already suffer from normally painful diseases as such replacement often requires manipulation of collars by the operator, with the risk of causing movements that are hazardous for the vertebrae of the patient and might affect the patient's physical recovery. Furthermore, in case of diseases that are not caused by head trauma but instead by cerebral anoxia or hypoxia, for example due to a cardiac arrest, the use of such collars can be inappropriate as the collars can immobilize the patient and hinder treatment or makes therapy useless.

BRIEF DESCRIPTION OF THE DRAWINGS

The drawings described herein are for illustration purposes only and are not intended to limit the scope of the present invention in any way.

FIG. 1 is a perspective schematic view of one embodiment of a therapeutic collar of the present invention in a first or closed configuration.

FIG. 2 is a front schematic view of the collar of FIG. 1 in a second or open configuration that provides a view of the interior of the collar.

FIG. 3 is a broken cross-sectional view of a portion of the collar of FIG. 1, as taken along the line 3-3 of FIG. 2.

DETAILED DESCRIPTION OF THE INVENTION

Figure 4:
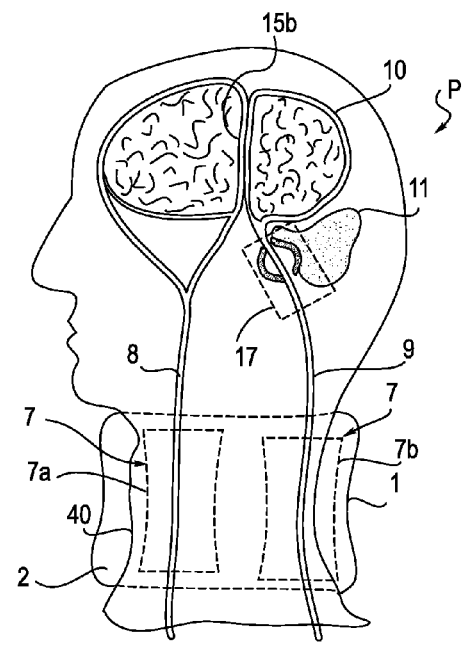
FIG. 4 is a highly schematic view of the head and neck of a patient wearing one embodiment of the therapeutic collar of the present invention.
Figure 5:
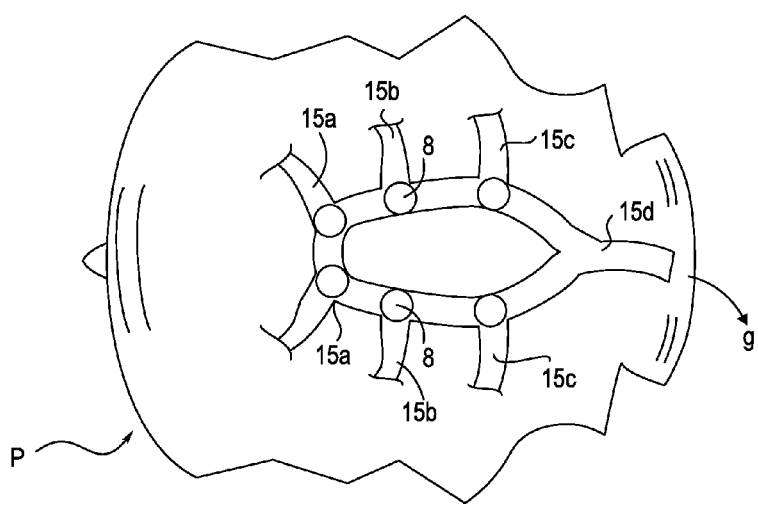
FIG. 5 is a highly schematic top view of a network of intracranial blood vessels, known as Circle of Willis, which supplies blood to the brain or encephalic region of a human being.

In one embodiment of the invention, a therapeutic collar of disposable type is provided that allows constant thermal treatment of the neck zone with the arteries that supply one or more of the brain 10, cerebellum 11 and other intracranial structures for as long as desired. In one embodiment, the collar can decrease its temperature to a desired value to induce hypothermia and preserve for a given time the cerebral functions of a patient after cerebral anoxia or hypoxia or other serious injuries of the cranial or encephalic region. In one embodiment, the temperature of the collar is decreased to a temperature ranging from 32.0 degrees C. (89.6 degrees F.) to 36.0 degrees C. (96.8 degrees F.), and in one embodiment the collar is decreased to a temperature of approximately 34.0 degrees C. (93.2 degrees F.). The collar can so operate both during first rescue operations and during the following therapies at the hospital. The therapeutic collar can be interfaced with a control unit, for example for controlling and adjusting the thermal conditions to be provided in contact with the patient's neck. The patient can be any suitable mammalian body, and in one embodiment is a human.

Referring now to FIGS. 1 to 5, numeral 1 generally designates a therapeutic collar or device, which in one embodiment is of a disposable type. Collar 1 can include an elongate body 2 having a longitudinal axis "A" and can have a front cut to define a dividing plane 2-2 that divides it into two sections 3 and 4, which can be ends. The first and second sections 3, 4 may be elastically opened apart to allow the collar 1 to be worn around the neck 40 of a patient "P" or to be removed. The neck 40 of the patient has a circumference, and the body 2 can have a length approximating the circumference of the neck of the patient. In one embodiment, the length of the body 2 ranges from 30 to 45 centimeters, in one embodiment the length of the body ranges from 35 to 40 centimeters and in one embodiment the length of the body is approximately 38 centimeters. The collar can be worn around at least a portion of the neck of the patient, and in one embodiment extends around the entire circumference of the neck of the patient. When positioned or mounted on the neck of the patient, the body 2 is arcuate or annular in shape. Body 2 can include an inner surface 2A adapted for engaging the neck 40 of the patient and an opposite outer surface 2B.

As mentioned above, the collar 1 can be made of a disposable and flexible material, such as any suitable cellular urethane for example Poron®. In one embodiment, the flexible material forms the inner portion 5A and the outer portion 5B of elongate body 2. The two ends 3 and 4 can be maintained in the closed state during use, using any suitable closure devices that are known to a person skilled in the art such as tear strips 6.

Cooling means or devices, generally referenced 7, are arranged in the body 2 such that, when the collar 1 is closed around the neck 40 and in an annular configuration, they are located at any or all of the carotid 8 and vertebral 9 arteries that extend along the neck 40 and supply blood to the cranial-encephalic region, that is the brain 10 and the cerebellum 11 and all other anatomical structures in the territories or areas of the carotid and vertebral arteries 8, 9 (see FIG. 4). In one embodiment, the cooling means indirectly affects the anterior cerebral arteries 15a, middle cerebral arteries 15b, posterior cerebral arteries 15c and basilar artery 15d (see FIG. 5), which are intracranial vessels, by acting on the carotid 8 and vertebral 9 arteries. The cooling means 7, which can also be referred to as refrigerating means, can be secured to the elongated body 2 by any suitable means. In one embodiment, the cooling means 7 are included in the flexible material of the body 2 at the time of polymerization or by the juxtaposition of an adhesive layer (not shown) between the cooling means external surface and the flexible material, for example where a cavity of the exact or approximate size and shape of the cooling means or element 7 has been created in the flexible material.

In one embodiment, a first plurality of at least two cooling means or assemblies 7a and a second plurality of at least two cooling means or assemblies 7b are carried by the elongate body. In one embodiment, the first and second plurality of cooling assemblies or devices 7 are spaced apart along the length of the elongate body so that the first plurality of at least two cooling devices or assemblies 7a overlie respectively the first plurality of two carotid arteries 8 and the second plurality of two cooling devices or assemblies 7b overlie respectively the second plurality of two vertebral arteries 9 when the elongate body is secured around the neck of the patient. In one embodiment, one cooling device or assembly 7 overlies each carotid artery 8 and one cooling device or assembly overlies each vertebral artery 9. As such, one cooling device or assembly 7a can overlie each of the two carotid arteries 8 extending through the neck 40 of the patient, and one cooling device or assembly 7b can overlie each of the two vertebral arteries 9 extending through the neck of the patient. The therapeutic collar or device 1 of the invention can include additional cooling devices or assemblies 7. For example, more than one cooling device or assembly can be provided for each of the carotid and vertebral arteries in the neck of the patient. For example, two or more cooling devices or assemblies 7 can overlie each or any of the carotid and vertebral arteries extending through the neck of the patient.

As shown in FIG. 2, the cooling means 7 may comprise, according to one embodiment, a plurality of thermoelectric devices or Peltier cells 12, which are placed in correspondence of or registration with the plurality of carotid and vertebral arteries to be affected by the collar. In one embodiment, the cooling means 7 are placed in spaced-apart position along the length of body 2 so as to accomplish such correspondence or registration. In one embodiment, each of the cooling means or devices 7 includes at least one Peltier cell or thermoelectric device 12, and in one embodiment each of the cooling means or devices 7 includes one Peltier cell or thermoelectric device 12.

In one embodiment, each of the cooling means or devices 7 may comprise a plurality of cooling tubes 13, and in one embodiment each of the cooling means or devices 7 includes at least one serpentine or other shaped tube 13. Such tubes 13 can each be adapted or configured to carry a temperature-controlled liquid flows, which liquid can be supplied by a pump unit 14 or any other suitable means and cooled to a predetermined temperature when provided to the collar 1, for example when the collar 1 is mounted around the neck 40 of a patient. It is appreciated that one or some of the cooling means 7, or all of the cooling means 7, may be a combination of thermoelectric devices 12 and at least one cooling tube 13. For example, in FIG. 2 each of the two cooling means 7 on the right of the elongate body 2 is a thermoelectric device 12 in combination with at least one cooling tube, for example at least one cooling tube 13 in a serpentine configuration. The at least one cooling tube 13 in any cooling means 7 may be in any other suitable configuration or shape, that is other than in a serpentine configuration.

The skilled person will understand that other solutions may be envisaged to make the cooling means 7. Such cooling means 7 can be positioned on the inner surface 2A of the collar body 2 so as to overlie one, any or all of the carotid arteries 8 and the vertebral arteries 9 (see FIG. 4 in particular) and thus provide a controlled hypothermia state in the blood that flows there through. The cooling of any or all of such arteries can serve to induce hypothermia in the circulatory system that supplies the brain of the patient, for example the entire brain or encephalic region of the patient.

In one embodiment of the collar 1 in which the cooling means 7 includes Peltier cells or thermoelectric device 12, for example as illustrated in FIGS. 1 and 3, apertures 16 can be provided for radiating out the heat generated by the heat transfer surfaces of the thermoelectric devices 12 facing opposite to the neck 40 when the collar 1 is mounted on the patient's neck.

Thermoelectric devices 12 are known to create two heat transfer surfaces, namely a cold surface 12A, in this case facing the neck 40 of the patient "P", and an opposite and parallel heat-generating surface 12B. In one embodiment of the invention, the heat generated at surface 12 can be discharged through the apertures 16 provided in body 2 of the collar 1.

Figure 9:
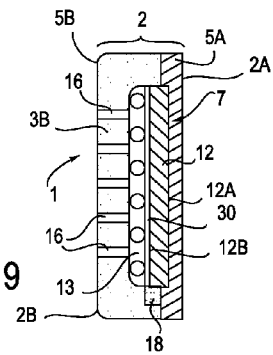
FIG. 9 is a schematic cross-sectional view of the therapeutic collar of FIG. 6, as taken along the line 9-9 of FIG. 8.

In one embodiment, the elongate body 2 includes an inner portion 5A for engaging the neck 40 of the patient and an outer portion 5B opposite the inner portion. The portions 5A and 5B, each of which can be formed from the flexible material discussed above, can be tightly joined together to form the scaffold of collar 2. In one embodiment, the inner portion 5A and the outer portion 5B can be joined together at the time of polymerization or by the juxtaposition of an adhesive layer (not shown) between them (see FIG. 9). The inner portion 5A can include inner surface 2A, and the outer portion 5B can include outer surface 2B. In one embodiment, the inner portion 5A is thermo-conductive, and is thus a thermo-conductive layer. In one embodiment, the inner portion 5A can be made from a material having a thermal conductivity ranging from 0.2 to 10.0 W/mK, in one embodiment the inner portion 5A or thermo-conductive layer can be made from a material having a thermal conductivity ranging from 0.2 to 0.5 W/mK and in one embodiment the inner portion 5A or thermo-conductive layer can be made from a material having a thermal conductivity ranging from one to two W/mK. The inner portion 5A can be made from any suitable material, such as a soft biocompatible polymer, an adhesive gel or a gel. In one embodiment, the outer portion 5B is thermo-insulating layer, and is thus a thermo-insulating layer. In one embodiment, the outer portion 5B can be made from a material having a thermal conductivity ranging from 0.01 to 0.19 W/mK and in one embodiment the outer portion 5B can be made from a material having a thermal conductivity ranging from 0.02 to 0.09 W/mK. The outer portion 5B can be made from any suitable material, such as soft biocompatible polymer, a foam or a polyurethane. The thermo-conductive inner portion 5A facilitates hypothermic exchange with the neck 40. The thermo-insulating outer portion 5B can inhibit the outer surface 2B of the collar 1 from becoming hot and possible dangerous to the user or others and can inhibit heat from the hot surface of the cooling means 7 from traveling through the elongate body 2 of the cold surface of the cooling means 7.

The cold surface of the cooling means 7 contacts or engages the inner portion 5A of elongate body 2 while the hot surface of the cooling means is in contact with or engages the outer portion 5B of the elongate body. Apertures 16 can be provided in the outer portion 5B to facilitate the removal of heat from the hot surface of the cooling means, devices or assemblies 7 (see FIG. 3). In one embodiment, where the cooling means 7 are formed by the coupling of a plurality of Peltier cells 12 with a respective plurality of cooling tubes 13, for example as discussed below, the cold surface of the Peltier cell 12 is in contact with the inner portion 5A of the elongate body 2, while the coupling of the hot surface of the Peltier cell 12 and the cooling tubes 13 are included in the outer portion 5B of the elongate body 2 (see FIG. 9). Heat-escape apertures 16 can be provided for each of the cooling means assemblies 7 having a Peltier cell 12 and at least one cooling tube 13 engaging the hot surface of the Peltier cell 12. In each case, the heat-removal features or structure in the outer portion 5B enhances the removal of heat from the hot surface of the Peltier device 12 so as to enhance the refrigerating efficiency of the cooling means 7.

Irrespective of whether the cooling means are in the form of Peltier cells 12 or serpentines 13, a combination of the foregoing or any other suitable arrangement, is the system of the invention can be provided with one or more temperature sensors 18 that can be connected to a control unit 19. The temperatures sensors 18 can be of any suitable type, for example a thermocouple or other electrical sensor. The control unit 19 can receive the electrical signals generated by the one or more temperature sensors and, in response thereto, change and maintain the temperatures of the cooling means 7 as needed or desired, for example to inhibit damage to the neck 40 during operation of the collar 1. Such damage could have included damage to the skin of the neck, for example to the skin underlying the cooling means 7. In one embodiment, a temperature sensor is carried by the elongate body 2 in the vicinity of each of the cooling means 7. In one embodiment, as illustrated in FIG. 2, a temperature sensor 18 is provided in the elongate body 2 adjacent to or within the confines of each cooling means 7. In one embodiment, temperature sensors 18 are provided in other areas of the patient's body, for example in, adjacent or near certain organs of the patient, and electrically coupled to the control unit 19 for monitoring the temperature of such one or more areas and providing feedback signals to the control unit 19 for use by the control unit to adjust or maintain the energy provided by the control unit to thermoelectric devices 12 on collar 1. Such one or more other temperature sensors 18 can be in addition to or in lieu of the one or more temperature sensors 18 on collar 1, and can be located in or near the patient's brain, esophagus or bladder or any combination of the foregoing. In one embodiment, a probe having a temperature sensor at or near the distal end thereof can be inserted into the brain. Invasive brain temperature measurement, for example by the insertion of a thermal probe into the brain tissue, can be direct and reliable technique to measure brain temperature. Esophagus and bladder can be suitable sites for the measurement of a proxy of the core temperature of the brain. The temperature of the esophagus and bladder are sometimes considered to be in equilibrium with the temperature of the brain. The temperature of the esophagus and bladder can be measured by any suitable means, for example by use of probes or other devices inserted into or nearby such organs. The combination of more techniques and sites for measuring body temperature, for example measuring the temperature of the brain, the esophagus, the bladder or any combination of the foregoing, can increase the accuracy of creating a desired hypothermia or temperature in the brain.

In one embodiment of the operation and use of the collar of the present invention, the collar is wrapped around all or at least a portion of the neck 40 of the patient. In one method of use, sections 3, 4 of the collar are placed at the rear of the neck and thus serve as the posterior portion of the collar, while the middle portion of the collar is placed at the front of the patient's neck and thus serves as the anterior portion of the collar. It is appreciated that sections 3, 4, or the opening portion of the collar 1, can be placed at the front of the patient's neck or elsewhere around the neck with the cooling means or devices 7 positioned on the elongate body 2 for registration with the neck arteries in the manner discussed herein. Electrical energy can then be supplied to one or more of the thermoelectric devices 12 of the collar that overlie one or more of the arteries carrying blood to the head of the patient so as to cool the blood passing through the arteries to a suitable temperature for inducing hypothermia in the circulatory system that supplies the brain. In one embodiment, the blood passing through such one or more arteries is cooled to a temperature ranging from 89.6 to 96.8 degrees Fahrenheit. In one embodiment, electrical energy is supplied to such one or more thermoelectric or Peltier devices so as to cool the skin overlying such one or more arteries to a temperature not less than 39.2 degrees Fahrenheit, for example in one embodiment to a temperature ranging from 41 to 55 degrees Fahrenheit. It is appreciated that the foregoing temperature ranges can be relevant to collars having cooling means or devices 7 that do not include thermoelectric or Peltier devices 12.

Figure 6:
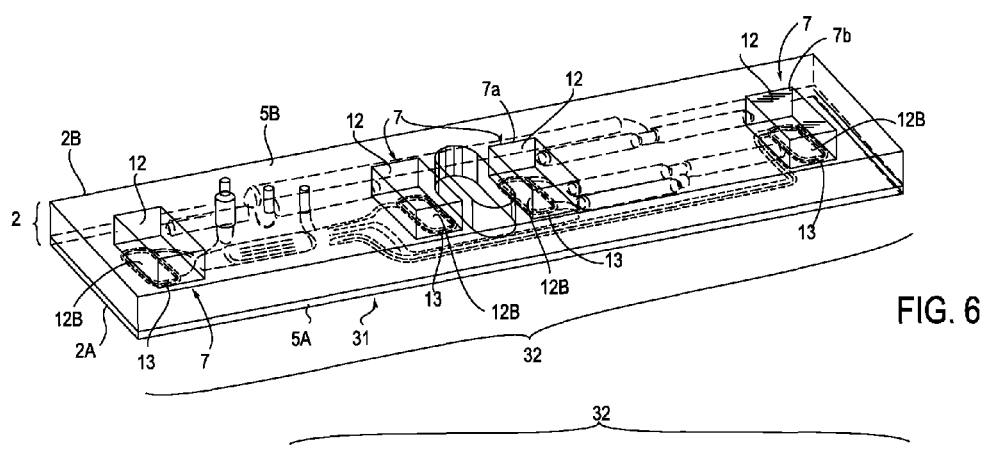
FIG. 6 is a highly schematic perspective and phantom view of a second embodiment of the collar of the present invention.
Figure 7:
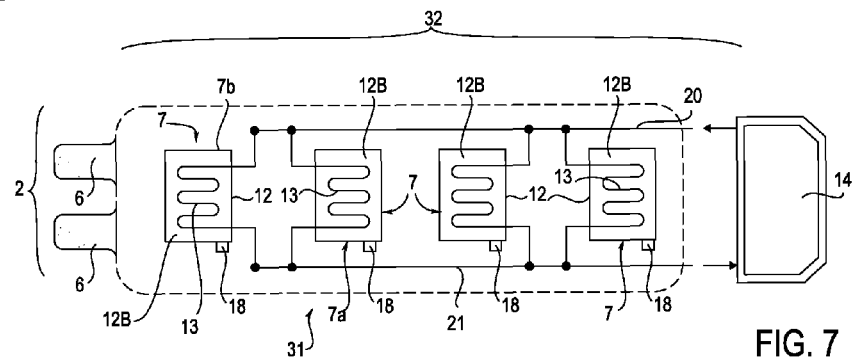
FIG. 7 is a small-scale schematic view of one embodiment of a connection arrangement between the cooling units of the collar of FIG. 6.
Figure 8:
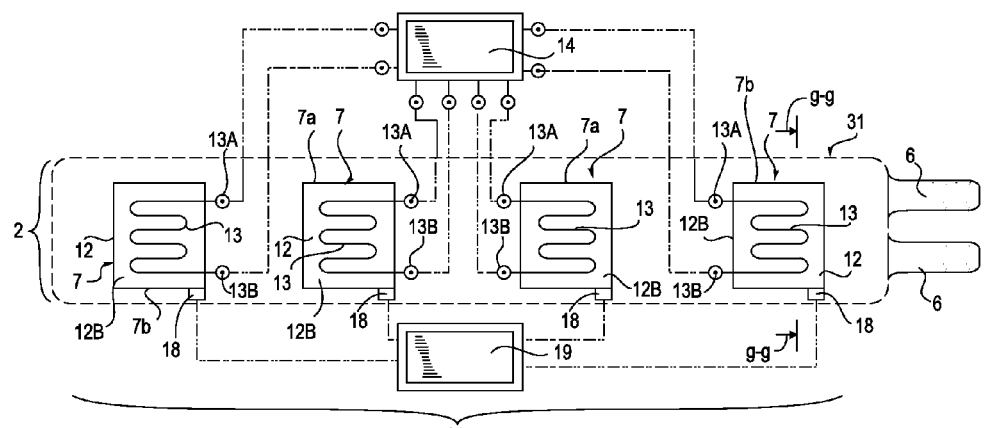
FIG. 8 is a schematic view of another embodiment of a connection arrangement between the cooling units of the collar of FIG. 6.

FIGS. 6 to 8 show a further possible embodiment of the collar of the invention. Collar 31 is similar to collar 1 and like reference numerals have been used to describe like components of collars 1 and 31. For example, collar 31 can include an inner portion 5A and an outer portion 5B, each of which can be made from any suitable material such as the flexible material discussed above.

In this embodiment, the cooling means or assemblies 7 can comprise a combination of thermoelectric devices 12, such as Peltier cells 12, and at least one cooling tube 13, such as in a serpentine or other suitable configuration, in close contact with each other. An optional layer of conductive gel 30, for example a gel containing metal salts, can be provided or interposed between each thermoelectric device 12 and related at least one cooling tube. In one embodiment, at least one cooling tube 13 is carried by the elongate body 32 of collar 31 for each thermoelectric device 12 and extends in the vicinity of such thermoelectric device 12 for removing heat from the thermoelectric device so as to enhance the cooling effect of the thermoelectric devices 12. In one embodiment, a cooling tube 13, for example in a serpentine configuration, overlies or is disposed adjacent to the heat-generating surface 12B of each thermoelectric device 12 for removing heat from such surface 12B. In one embodiment, such serpentine configuration is within the confines of heat generating surface 12B. The effectiveness of thermoelectric coolers or devices 12 is enhanced when there is a large temperature differential between the cold side 12A and the hot side 12B of the device 7. The inclusion of a high capacity second cooling means, such as a serpentine of cooling tubes 13 carrying cooling fluids for removing heat from the hot side 12B of the thermoelectric device or apparatus 12, can increase the temperature differential between sides 12A and 12B by causing a lower temperature on cold side 12A and thus increase the effectiveness of devices 12 and collar 31.

Each at least one cooling tube 13 pertaining to a thermoelectric device 12, for example each serpentine-configured cooling tube 13, has an inlet 13A and an outlet 13B for respectively receiving and discharging cooling fluid flowing through such cooling tube.

In one embodiment, each inlet 13A and outlet 13B may be connected in parallel to corresponding cooling fluid lines 20 and 21, for example as shown in FIG. 7, which are in turn may be connected to a pump unit 14. In this manner, the cooling tubes 13 are not connected in series, and the cooling fluid from one cooling tube 13 is not utilized by another cooling tube so as to decrease the efficiency of each cooling tube 13. The parallel configuration of the cooling tubes 13 and the connection of each cooling tube to the pump unit facilitates that fluid at the same temperature is supplied to each thermoelectric device 12. In one embodiment, each inlet 13A and outlet 13B may be directly connected to the pump unit, for example as shown in FIG. 8.

In one embodiment, the cooling units 7 of collar may also equipped with temperature sensors 18, such as of the type discussed above, which in turn may be electrically connected with the control unit 19, which can receive and analyze the data received from the sensors 18 and automatically adjust or control the temperature of the cooling fluids being supplied by the pump unit 14 to the cooling tubes. In one embodiment, a temperature sensor is carried by the elongate body 32 in the vicinity of each of the cooling means or units 7. In one embodiment, as illustrated in FIG. 8, a temperature sensor 18 is provided in the elongate body 32 adjacent to or within the confines of each cooling means 7. One or more temperature sensors for monitoring the temperature in one or more other areas of the patient's body can be utilized with collar 31, for example as discussed above with respect to collar 1.

It is appreciated that in the embodiment in which the tube inlets 13A and tube outlets 13B are connected in parallel with each other, and in the embodiment in which inlets 13A and outlets 13B are independently connected to the pump unit 14, the temperature changes of the cooling fluids that circulate in the cooling tubes 13 are negligible.

In operation and use, collar 31 can be operated in a manner similar to the operation of collar 1 discussed above. In this regard, numeral 17 in FIG. 4 schematically designates the center of the brain that controls the vital functions of the patient "P." The temperature of such center or area 17, located in the occipital region close to the cerebellum 11, can be maintained in a hypothermic state by the collar 1, if required, to avoid brain damage in case of hypoxia or anoxia, irrespective of the cause of these states in the patient "P". At least some of the cooling elements or devices 7 of the invention, including for example at least some of thermoelectric devices 12, can be utilized to cool the respective arteries which such devices overlie to induce hypothermia in the circulatory system that supplies the brain.

In one embodiment, a therapeutic collar for use by a patient having a neck with a circumference and a first plurality of two carotid arteries and a second plurality of two vertebral arteries extending through the neck to the brain is provided. The therapeutic collar can include an elongate body adapted for engaging the neck of the patient, the body being made from a flexible material for extending around at least a portion of the neck and having a length approximating the circumference of the neck, a first plurality of two thermoelectric devices and a second plurality of two thermoelectric devices carried by the elongate body and spaced apart along the length of the elongate body so that the first plurality of two thermoelectric devices overlie respectively the first plurality of two carotid arteries and the second plurality of two thermoelectric devices overlie respectively the second plurality of two vertebral arteries when the elongate body is secured around the neck of the patient, at least one cooling tube carried by the elongate body and extending in the vicinity of each of the thermoelectric devices for removing heat from the thermoelectric devices so as to enhance the cooling effect of the thermoelectric devices whereby at least some of the first and second plurality of two thermoelectric devices can be utilized to cool the respective arteries and thus induce hypothermia in the circulatory system that supplies the brain.

The elongate body can include an inner portion for engaging the neck, the inner portion including a thermo-conductive layer. The thermo-conductive layer can be made from a material having a thermal conductivity ranging from 0.2 to 10.0 W/mK. The thermo-conductive layer can be made from a material selected from the group consisting of a soft biocompatible polymer and an adhesive gel. The elongate body can include an outer portion opposite the inner portion, the outer portion including a thermo-insulating layer. The thermo-insulating layer can be made from a material having a thermal conductivity ranging from 0.01 to 0.19 W/mK. The thermo-insulating layer can be made from a material selected from the group consisting of a soft biocompatible polymer, a foam and polyurethane. The flexible material can be selected from the group consisting of polyurethane, silicon and rubber. The therapeutic collar can include a temperature sensor carried by the elongate body in the vicinity of each thermoelectric device for inhibiting damage to the neck during cooling. The temperature sensor can be adjacent the thermoelectric device. The at least one cooling tubes extending in the vicinity of each of the thermoelectric devices can extend in parallel. The at least one cooling tubes extending in the vicinity of each of the thermoelectric devices can have respective inlet and outlet ends for coupling directly to a pump.

In one embodiment, a system for inducing hypothermia in a brain of a patient having a neck with two carotid arteries and two vertebral arteries extending through the neck to the brain is provided. The system can include an elongate body adapted for engaging the neck of the patient, the body being made from a flexible material for extending around at least a portion of the neck, a plurality of at least four thermoelectric devices carried by the elongate body and spaced apart along the length of the elongate body so that the thermoelectric devices overlie respective arteries when the elongate body is secured around at least a portion of the neck of the patient, a temperature sensor carried by the elongate body in the vicinity of each thermoelectric device and a controller electrically coupled to the thermoelectric devices and the temperature sensors for selectively providing electric energy to the thermoelectric devices so as to cool the respective arteries and thus induce hypothermia in the circulatory system that supplies the brain and for obtaining feedback from the temperatures sensors so as to monitor temperatures of the neck in the vicinity of the thermoelectric devices to inhibit damage to the neck during cooling.

The system can include at least one additional temperature sensor separate from the elongate body and electrically coupled to the controller for monitoring the temperature of another portion of the patient during cooling. The additional temperature sensor can include a temperature sensor configured to monitor the temperature of the brain, esophagus or bladder of the patient.

In one embodiment, a method for inducing hypothermia in a patient having a neck with two carotid arteries and two vertebral arteries extending through the neck to the brain is provided. The method can include the steps of applying electrical energy to a plurality of four thermoelectric devices each engaging the neck at a position overlying one of the arteries so as to cool blood passing through the arteries and thus induce hypothermia in the circulatory system that supplies the brain and monitoring the temperature of the neck nearby the thermoelectric devices with an electrical sensor so as to inhibit damage to the skin nearby the thermoelectric devices during cooling.

The method can include monitoring the temperature of organs within the patient and adjusting the electrical energy being applied to at least some of the plurality of thermoelectric devices in response to the monitored temperatures of the organs. The organs can be selected from the group consisting of the stomach, the esophagus and the bladder.

The applying step can include applying electrical energy to a plurality of four thermoelectric devices each engaging the neck at a position overlying one of the arteries so as to cool blood passing through the arteries to a temperature ranging from 89.6 to 96.8 degrees Fahrenheit. The applying step can include applying electrical energy to a plurality of four thermoelectric devices each engaging the neck at a position overlying one of the arteries so as to cool the skin overlying the arteries to a temperature not less than 39.2 degrees Fahrenheit. The applying step can include applying electrical energy to a plurality of four thermoelectric devices each engaging the neck at a position overlying one of the arteries so as to cool the skin overlying the arteries to a temperature ranging from 41 to 55 degrees Fahrenheit.

In one embodiment, a therapeutic collar designed to be fitted around the neck of a patient is provided. The collar can include an annular body having a longitudinal axis and comprising two sections that can be parted reciprocally and defining a front section and a rear section and two side connecting zones, a dividing plane between said sections; a closing and opening device of said two sections, a reciprocally coaxial inner wall and an outer wall of said annular body, first refrigerating means fitted in correspondence of said front section, and second refrigerating means associated to said inner wall in correspondence of at least said side and rear sections, characterized in that said first and second refrigerating means comprise a plurality of refrigeration units, each refrigeration unit comprising a coupling in a close contact between a Peltier cell and a corresponding cooling coil wherein refrigerating fluids feed by feeding means flow.

The second refrigerating means can include constant refrigerating means. The cooling coils can have respective inlet and outlet ends of said refrigerating fluids, which reciprocally are connected in parallel. The cooling coils can have respective inlet and outlet ends of said refrigerating fluids, which reciprocally independently connected with a pumping group. The annular body can include heat removal means coming from said Peltier cell toward the outside. The second refrigerating means can be associated to said inner wall to contact zones wherein, for example, carotid arteries and vertebral arteries pass. The collar can include an outer thermo-insulating portion and an inner thermo-conductive portion. The dividing plane can be parallel to said longitudinal axis. At least a layer of a conductive material can be interposed between said Peltier cell and cooling coils. The conductive material can include a gel containing metallic salts. Each of said refrigeration units can include an automatic temperature control sensing means.

The invention has been found to fulfill the intended objects.

The invention as conceived is susceptible to changes and variants within the inventive concept.

Also, all the details may be replaced by other technical equivalent elements.

In its practical implementation, any material, shape and size may be used as needed, without departure from the scope as defined by the following claims.

The therapeutic collar of the present invention is advantageous in many respects. In this regard, for example, the therapeutic collar is disposable, easily wearable and comfortable for patients. The therapeutic collar can maintain the neck of a patient at a desired and substantially constant temperature, for a desired and extended interval of time, without any degradation of thermal treatment. In one embodiment, the therapeutic collar requires no displacement of the patient to prepare the required thermal treatment.

I claim:

1. A therapeutic collar for use by a patient with a brain injury having a neck and two carotid arteries and two vertebral arteries extending through the neck to anterior cerebral arteries, middle cerebral arteries, posterior cerebral arteries and a basilar artery in a brain, comprising an elongate body adapted for engaging the neck of the patient, the body being made from a flexible material for extending around at least a portion of the neck, a first plurality of two independently-controlled thermoelectric devices and a second plurality of two independently-controlled thermoelectric devices carried by the elongate body, the first plurality of two thermoelectric devices being spaced apart along the length of the elongate body from the second plurality of two thermoelectric devices so that the first plurality of two thermoelectric devices can overlie and selectively cool each of the two carotid arteries and the second plurality of two thermoelectric devices can overlie and selectively cool each of the two vertebral arteries when the elongate body is secured around the neck of the patient, the selective cooling of the two carotid arteries by the first plurality of two independently-controlled thermoelectric devices and the selective cooling of the two vertebral arteries by the second plurality of two independently-controlled thermoelectric devices when the elongate body is secured around the neck of the patient causing controlled cooling of the anterior cerebral arteries, the middle cerebral arteries, the posterior cerebral arteries and the basilar artery so as to induce hypothermia in the brain of the patient.

2. The therapeutic collar of claim 1, wherein the elongate body includes an inner portion for engaging the neck, the inner portion including a thermo-conductive layer.

3. The therapeutic collar of claim 2, wherein the thermo-conductive layer is made from a material having a thermal conductivity ranging from 0.2 to 10.0 W/mK.

4. The therapeutic collar of claim 3, wherein the thermo-conductive layer is made from a material selected from the group consisting of a soft biocompatible polymer and an adhesive gel.

5. The therapeutic collar of claim 2, wherein the elongate body includes an outer portion opposite the inner portion, the outer portion including a thermo-insulating layer.

6. The therapeutic collar of claim 5, wherein the thermo-insulating layer is made from a material having a thermal conductivity ranging from 0.01 to 0.19 W/mK.

7. The therapeutic collar of claim 6, wherein the thermo-insulating layer is made from a material selected from the group consisting of a soft biocompatible polymer, a foam and polyurethane.

8. The therapeutic collar of claim 1, wherein the flexible material is selected from the group consisting of polyurethane, silicon and rubber.

9. The therapeutic collar of claim 1, further comprising a plurality of temperature sensors carried by the elongate body with one of the plurality of temperature sensors in the vicinity of each thermoelectric device for inhibiting damage to the neck during cooling.

10. The therapeutic collar of claim 9, wherein each one of the plurality of temperature sensors is adjacent the respective thermoelectric device.

11. The therapeutic collar of claim 1, further comprising a plurality of cooling tubes carried by the elongate body with at least one of the plurality of cooling tubes extending in the vicinity of each of the thermoelectric devices for removing heat from the thermoelectric devices so as to enhance the cooling effect of the thermoelectric devices.

12. The therapeutic collar of claim 11, wherein the plurality of cooling tubes extend in parallel.

13. The therapeutic collar of claim 12 for use with a pump, wherein each of the plurality of cooling tubes has an inlet end and an outlet end for coupling directly to the pump.

14. The therapeutic collar of claim 11, wherein each of the thermoelectric devices has a cold surface and an opposite heat-generating surface and wherein at least one of the plurality of cooling tubes is disposed adjacent the heat-generating surface of each of the thermoelectric devices for removing heat from the thermoelectric devices so as to enhance the cooling effect of the thermoelectric devices.

15. A system for inducing hypothermia in a patient with a brain injury having a neck and two carotid arteries and two vertebral arteries extending through the neck to anterior cerebral arteries, middle cerebral arteries, posterior cerebral arteries and a basilar artery in a brain, comprising an elongate body adapted for engaging the neck of the patient, the body being made from a flexible material for extending around at least a portion of the neck, a first plurality of two independently-controlled thermoelectric devices and a second plurality of two independently-controlled thermoelectric devices carried by the elongate body and spaced apart along the length of the elongate body so that the first plurality of two thermoelectric devices overlie and selectively cool each of the two carotid arteries and the second plurality of two thermoelectric devices overlie and selectively cool each of the two vertebral arteries when the elongate body is secured around at least a portion of the neck of the patient and a controller electrically coupled to the thermoelectric devices, the controller being configured to selectively cause the thermoelectric devices to provide controlled cooling of the anterior cerebral arteries, the middle cerebral arteries, the posterior cerebral arteries and the basilar artery so as to induce hypothermia in the brain of the patient.

16. The system of claim 15, further comprising a plurality of temperature sensors carried by the elongate body with one of the plurality of temperature sensors being in the vicinity of each one of the thermoelectric devices.

17. The system of claim 15, further comprising at least one additional temperature sensor separate from the elongate body and electrically coupled to the controller for monitoring the temperature of another portion of the patient during cooling.

18. The system of claim 15, wherein the controller is configured to selectively cause the thermoelectric devices to provide hypothermia-inducing cooling in the range of 89.6° F. to 96.8° F. to the respective arteries.

19. A therapeutic collar for use with a controller by a patient with a brain injury having a neck and two carotid arteries and two vertebral arteries extending through the neck to anterior cerebral arteries, middle cerebral arteries, posterior cerebral arteries and a basilar artery in a brain, comprising an elongate body adapted for engaging the neck of the patient, the body being made from a flexible material for extending around at least a portion of the neck, a first plurality of two independently-controlled thermoelectric devices and a second plurality of two independently-controlled thermoelectric devices carried by the elongate body and adapted for electrical coupling to the controller, the thermoelectric devices being spaced apart along the length of the elongate body so that the first plurality of two thermoelectric devices overlie and selectively cool each of the two carotid arteries and the second plurality of two thermoelectric devices overlie and selectively cool each of the two vertebral arteries when the elongate body is secured around at least a portion of the neck of the patient, the selective cooling of the two carotid arteries by the first plurality of two independently-controlled thermoelectric devices and the selective cooling of the two vertebral arteries by the second plurality of two independently-controlled thermoelectric devices causing controlled cooling of the anterior cerebral arteries, the middle cerebral arteries, the posterior cerebral arteries and the basilar artery so as to induce hypothermia in the brain of the patient and a plurality of temperature sensors carried by the elongate body and adapted for electrical coupling to the controller, one of the plurality of temperature sensors being adjacent each one of the thermoelectric devices whereby the controller selectively controls the thermoelectric devices and obtains feedback from each of the temperatures sensors so as to monitor temperatures of the neck in the vicinity of each of the thermoelectric devices and control the electrical energy being provided to the thermoelectric devices so as to inhibit damage to the neck from the thermoelectric devices.

20. The therapeutic collar of claim 19, wherein the one of the plurality of temperature sensors is within the confines of each thermoelectric device.

\* \* \* \* \*